United States Patent
Ramesan et al.

(10) Patent No.: US 11,707,429 B2
(45) Date of Patent: Jul. 25, 2023

(54) METHOD AND DEVICE FOR ACOUSTICALLY MEDIATED INTRACELLULAR DELIVERY

(71) Applicant: Royal Melbourne Institute of Technology, Melbourne (AU)

(72) Inventors: Shwathy Ramesan, Lalor (AU); Amgad Rezk, Bayswater (AU); Leslie Yeo, Malvern East (AU)

(73) Assignee: ROYAL MELBOURNE INSTITUTE OF TECHNOLOGY, Melbourne (AU)

( * ) Notice: Subject to any disclaimer, the term of this patent is extended or adjusted under 35 U.S.C. 154(b) by 471 days.

(21) Appl. No.: 16/758,988

(22) PCT Filed: Oct. 26, 2018

(86) PCT No.: PCT/AU2018/051154
§ 371 (c)(1),
(2) Date: Apr. 24, 2020

(87) PCT Pub. No.: WO2019/079857
PCT Pub. Date: May 2, 2019

(65) Prior Publication Data
US 2021/0177737 A1    Jun. 17, 2021

(30) Foreign Application Priority Data
Oct. 26, 2017   (AU) ................................ 2017904333

(51) Int. Cl.
| | |
|---|---|
| A61K 9/00 | (2006.01) |
| C12N 5/00 | (2006.01) |
| B06B 1/06 | (2006.01) |

(52) U.S. Cl.
CPC .......... *A61K 9/0009* (2013.01); *C12N 5/0068* (2013.01); *B06B 1/06* (2013.01); *C12N 2521/10* (2013.01)

(58) Field of Classification Search
CPC ................ A61K 9/0009; C12N 5/0068; C12N 2521/10; B06B 1/06; B82Y 5/00
See application file for complete search history.

(56) References Cited

U.S. PATENT DOCUMENTS

| | | |
|---|---|---|
| 6,679,436 B1 | 1/2004 | Onishi et al. |
| 2012/0097752 A1 | 4/2012 | Okano et al. |
| 2017/0128898 A1 | 5/2017 | Okano et al. |

FOREIGN PATENT DOCUMENTS

| | | | |
|---|---|---|---|
| CN | 102981090 A | 3/2013 | |
| CN | 103981090 A * | 8/2014 | ............ C12M 23/16 |

(Continued)

OTHER PUBLICATIONS

IP.com search (Year: 2022).*

(Continued)

*Primary Examiner* — Lisa Solomon
(74) *Attorney, Agent, or Firm* — Westman, Champlin & Koehler, P.A.

(57) ABSTRACT

An intracellular delivery device (1) including, a piezoelectric substrate (3) having a working surface (8), at least one interdigitated transducer (5) located on and in contact with the working surface (8), and a receptacle (11) located on the working surface for accommodating cells to be targeted for intracellular delivery therein, wherein an alternating signal applied to the interdigitated transducer generates acoustic wave energy through the piezoelectric substrate that can be transferred to the accommodated cells.

20 Claims, 12 Drawing Sheets

(56) References Cited

FOREIGN PATENT DOCUMENTS

| CN | 103981090 A | 8/2014 |
|---|---|---|
| JP | 2004190537 A | 7/2004 |
| WO | 2005056104 A2 | 6/2005 |
| WO | 2010129994 A1 | 11/2010 |
| WO | 2014132228 A1 | 9/2014 |
| WO | 2016179664 A1 | 11/2016 |
| WO | 2017173478 A1 | 12/2017 |

OTHER PUBLICATIONS

Amgad R. Resk et al., "HYbriD Resonant Acoustics (HYDRA)", Advanced Materials, 2016, vol. 28, pp. 1970-1975.
International Search Report in corresponding PCT Application PCT/AU2018/051154, dated Dec. 11, 2018.
Kurosawa M. et al., "Surface acoustic wave atomizer", Sensors and Actuators A, vol. 50, issues 1-2, Aug. 1995 pp. 69-74.
Qi A. et al., "A Miniaturized Surface Acoustic Wave Atomizer with a Disposable Pump-free Liquid Supply System for Continuous Atomization", Proceedings of the 2011 6th IEEE International Conference on Nano/Micro Engineered and Molecular Systems, Kaohsiung, Taiwan, Feb. 20-23, 2011, pp. 295-298.
Yoon S, et al. "Direct and sustained intracellular delivery of exogenous molecules using acoustic-transfection with high frequency ultrasound", Scientific Reports, Feb. 4, 2016, pp. 1-11.
Yoon S. et al. "Acoustic-transfection for genomic manipulation of single-cells using high frequency ultrasound", Scientific Reports, Jul. 13, 2017, pp. 1-11.

* cited by examiner

METHOD AND DEVICE FOR ACOUSTICALLY MEDIATED INTRACELLULAR DELIVERY

CROSS-REFERENCE TO RELATED APPLICATION(S)

The present application is a § 371 national phase entry of and claims priority of International patent application Serial No. PCT/AU2018/051154, filed Oct. 26, 2018, and further claims priority to Australian Patent application No. 2017904333, filed Oct. 26, 2017, the content of which is hereby incorporated by reference in its entirety.

FIELD OF THE INVENTION

The present invention is directed to intracellular delivery methods and devices for research and therapeutic purposes.

BACKGROUND OF THE INVENTION

The insertion of therapeutic and imaging agents such as nucleic acids, peptides, proteins, nano-/molecular probes and nanoparticles, among others, into cells represents a crucial step in many of the next generation strategies currently being developed to diagnose and treat a variety of diseases (gene/cell therapy, gene editing, stem cell reprogramming or various theranostic approaches, as examples). The internalisation of these exogenous materials, however, is severely restricted by the barrier imposed by the hydrophobic and apolar nature of the lipid bilayer that constitutes the cell membrane. As such, considerable effort has been dedicated to investigating the use of either physical (membrane-disruption-mediated) or biochemical (carrier-mediated) methods to facilitate easier intracellular transport through the lipid bilayer.

Examples of physical membrane disruption mediated methods include electroporation, sonoporation and microinjection, in which physical forces are exploited to disrupt the structure of the cell membrane, particularly through the formation of pores. While this allows a wide range of submicron particulate matter to be delivered into the cell, a downside of a large proportion of these methods, however, lies in the damage inflicted on the cells during the poration process. Electroporation, for example, which necessitates the application of high electric potentials across the cell membrane, often results in irreversible damage to the cell membrane, leading to a loss in homeostasis in the cell, and eventually apoptosis. Sonoporation, on the other hand, primarily exploits the cavitation of microbubbles induced by sound waves near the cell membrane to enhance its permeabilisation. Given that the mechanical stress arising from a single oscillating microbubble alone has been found to be sufficient to cause profound membrane damage to the cell wall, it is therefore likely that considerable cell death occurs due to the enormous stress the cells are subject to as a consequence of the intense shock waves and accompanying microjets generated during a cavitation event. Additionally, cells have been shown to suffer from post-cavitation DNA damage due to the production of reactive oxygen species (ROS) as a result of free radical formation during cavitation. The poor reseeding viability and colony-forming ability of cells following exposure to ultrasonic radiation has also been documented.

Biochemical carrier-mediated methods, on the other hand, which involve the use of viral or non-viral (for example, peptides, vesicles or nanoparticles) vectors to enhance cellular uptake via various endocytotic pathways do not exact such a detrimental burden on the cells. However, they often result in high local concentrations of the nanoparticle cargo within endosomal compartments, which eventually fuse with the lysosomes. Bar their rare (<1%) ability to escape this endosomal recycling pathway such that they are able to enter the cytoplasm where intracellular pathways exist to traffic the nanoparticles to the nucleus, the majority of the therapeutic cargo ends up in the lysosome, whose highly acidic and enzyme-rich environment leads to their degradation. A strategy that allows endosomal and lysosomal escape, or, better, avoidance of these organelles through a direct pathway into the cytosol is thus often necessary to enhance nuclear uptake of the therapeutic cargo leading to improved transfection efficiencies.

When using sonoporation, optimal transfections for mammalian cells have been achieved with ultrasound (which will be referred to as 'bulk acoustic waves' (BAW)) in the range of between 1-3 MHz. However, as noted above, the use of acoustic cavitation of microbubbles to modify the permeability of the cell plasma membrane can damage the cell leading to cell death. An alternative method using very high frequency (VHF) BAW, over 150 MHz, has been proposed that can deliver gene and proteins into cytoplasm without the use of microbubbles. See Sangpil Yoon et al, 'Direct and sustained intracellular delivery of exogenous molecules using acoustic-transfection with high frequency ultrasound', Scientific Reports 6, Article number: 20477 (2016) doi: 10.1038/srep20477', and 'Sangpil Yoon et al, 'Acoustic-transfection for genomic manipulation of single-cells using high frequency ultrasound', Scientific Reports 7, Article number: 5275 (2017) doi:10.1038/s41598-017-05722-1'. This method requires VHF BAW to be focused using an ultrasonic transducer probe onto a single cell into a diameter of 10 µm or less. While this technique can potentially lead to increased cell viability, it does have a number of practical disadvantages. Because much higher frequencies of over 150 MHz are used, it is necessary to bring the probe closer to individual cells. This is because as the frequency increases, the faster the acoustic wave attenuates over distance in the fluid; the attenuation length exponentially decreases with increasing frequency. This therefore requires a skilled operator using a microscope to locate a target cell in situ and to move the probe close to that cell within an accuracy of tens of microns. The distance from the cell needs to be controlled to ensure that the cell is influenced by the acoustic radiation from the probe, while not too close to prevent cell damage. Further, we note that the sharp gradient over which the acoustic wave attenuates that arises due to the high frequency typically generates localised heating effects which can adversely affect cells, some of which are susceptible to heat shock. In addition, cells need to be targeted one by one due to the confinement of the acoustic beam, making it very time consuming for large cell numbers, and therefore impractical to use on a commercial scale.

The above discussion of background art is included to explain the context of the present invention. It is not to be taken as an admission that the background art was known or part of the common general knowledge at the priority date of any one of the claims of the specification.

SUMMARY OF THE INVENTION

It would therefore be advantageous to provide a simple method and device that allows for efficient intercellular delivery of therapeutic molecules and nanoparticles to a large number of cells at one time, while at the same time maintaining a high level of cell viability.

With this in mind, according to one aspect of the present invention, there is provided an intracellular delivery device including, a piezoelectric substrate having a working surface, at least one interdigitated transducer located on and in contact with the working surface, and a receptacle located on the working surface for accommodating cells to be targeted for intracellular delivery therein, wherein an alternating signal applied to the interdigitated transducer generates acoustic wave energy through the piezoelectric substrate that can be transferred to the accommodated cells.

In another aspect, the present invention provides an intracellular delivery device including, a piezoelectric substrate having a working surface, at least one interdigitated transducer located on and in contact with the working surface, and a receptacle located on the working surface for accommodating a cell media;
the cell media comprising a plurality of cells to be targeted for intracellular delivery; and
therapeutic molecules or nanoparticles to be transferred by intracellular delivery into the cells;
wherein an alternating signal applied to the interdigitated transducer generates acoustic wave energy through the piezoelectric substrate that can be transferred to the plurality of cells.

The acoustic wave energy is preferably propagated as a surface acoustic wave (SAW) along the working surface. The acoustic wave energy is preferably further propagated as a surface reflected bulk wave (SRBW) within the piezoelectric substrate and internally reflected between the working surface and an adjacent surface of the piezoelectric substrate. SRBW can be generated when SAW on the working surface internally reflects between the working and adjacent surface of the piezoelectric substrate. SRBW will therefore be generated at the same frequency as the SAW. Therefore, reference to the application of SAW in the present application can also encompass the application of SRBW when present within the substrate. Further information on SRBWs can be found in International Publication No. WO 2016/179664 (RMIT University).

The at least one interdigitated transducer may be adapted to propagate surface acoustic waves having a frequency of greater than 10 MHz, and preferably a frequency of about 30 MHz.

The receptacle may have a base wall acoustically coupled to the working surface. A coupling medium may be provided between the working surface and the receptacle base wall to facilitate acoustic coupling therebetween. The coupling medium may be a silicone oil layer. It is also envisaged that there be a direct coupling of the working surface to the cell media where the receptacle does not have a base wall, and the cell media directly contacts the working surface.

The receptacle preferably includes a plurality of wells for accommodating therein the cell media. The piezoelectric substrate is preferably formed from lithium niobate (LiNbO$_3$), although the use of alternative piezoelectric materials is also envisaged.

According to another aspect of the present invention, there is provided an intracellular delivery method, including exposing a cell media including plurality of cells to be targeted for intracellular delivery, and therapeutic molecules and/or nanoparticles for said intracellular delivery therein, to acoustic wave energy including surface acoustic waves.

In a further aspect, the present invention provides an intracellular delivery method comprising exposing a cell media to acoustic wave energy including surface acoustic waves,
the cell media comprising a plurality of cells; and
therapeutic molecules and/or nanoparticles;
wherein the therapeutic molecules and/or nanoparticles are transferred into the exposed cells by intracellular delivery.

The acoustic wave energy preferably further includes surface reflected bulk waves.

The method may include exposing the cell media to acoustic energy generated by surface acoustic waves having a frequency greater than 10 MHz. More specifically, the method may include exposing the cell media to acoustic energy generated by surface acoustic waves having a frequency of about 30 MHz.

The cell media may be exposed for at least 30 seconds. More specifically, the cell media may be exposed for 5 minutes. Alternatively, the cell media may be exposed for 10 minutes.

The present invention shows that exposure of the cells to a short duration of high frequency (preferably >10 MHz) acoustic wave excitation induces an acoustic radiation on, and possibly resonant modes in the lipid structure of the cell membrane to facilitate the creation of transient and rapidly self-healing nanopores that are not only able to nonlinearly enhance the internalisation of, for example, gold nanoparticles into the cell, which are particularly difficult to deliver, by four-fold to five-fold in just several minutes whilst preserving a high level of cell viability (>97%), but also circumventing the need for endosomal strategies given that the nanoparticles are uniformly distributed throughout the cytosol. The internalisation of siRNA in the cell was also explored with the application of the aforementioned waves. The siRNA was internalised twice as much when the cells were exposed to the acoustic wave excitation compared to the control experiment in which the acoustic waves were absent. As expected, the siRNA were also present throughout the cytosol rather than in the endosomal and lysosomal compartments of the cell. Further and fluorescently labelled (FITC) dextran molecules of three different molecular weights corresponding to an approximate stokes radii of 3.3 nm, 6 nm and 10 nm, respectively, were also examined in which a two-fold increase was observed in the internalisation of the lowest molecular weight dextran (20 kDa) and a one and one half times increase for the 70 kDa and 250 kDa dextran, respectively, when exposed to the acoustic wave as compared to the control.

BRIEF DESCRIPTION OF THE DRAWINGS

It will be convenient to further describe the invention with respect to the accompanying drawings which illustrate a preferred embodiment of an acoustically-mediated intracellular delivery device and method according to the present invention. Other embodiments of the invention are possible, and consequently, the particularity of the accompanying drawings is not to be understood as superseding the generality of the preceding description of the invention.

In the drawings.

DETAILED DESCRIPTION OF THE INVENTION

The present invention provides a novel approach to enhance intracellular delivery of therapeutic molecules and nanoparticles (as nanocarriers for therapeutics and diagnostics), whilst maintaining a high level of cell viability. In the context of the present invention, the term "intracellular delivery" and variations thereof, refers to the transport of chemical or biological molecules (such as therapeutic molecules and nanoparticles) across the cell membrane into the cell. In the case of the present invention, this is achieved by exposing the cells to surface acoustic waves (SAW)—high frequency (>10 MHz) electromechanical Rayleigh waves, and preferably also surface reflected bulk waves (SRBW). SAW and SRBW, which unlike its low frequency (<1 MHz) bulk acoustic wave (BAW) counterpart used in sonoporation, does not result in cavitation or excessive shear denaturation. Importantly, unlike biochemical (carrier-mediated) methods for enhancing intracellular delivery (for example, use of viral or non-viral (such as plasmid DNA, calcium phosphate or cationic polymers) vectors), or even some physical (membrane-disruption) methods (for example, sonoporation, electroporation, gene gun, microinjection, etc.) where endocytosis constitutes the dominant internalisation mechanism, it is observed in the method according to the present invention that the majority of the delivered therapeutic molecules or nanoparticles are uniformly distributed throughout the cytosol instead of accumulating in the endosomal and lysosomal compartments. This is significant because once the molecules/nanoparticles are trapped within the endosomes (which eventually fuse with the lysosomes), their escape from the endosomal recycling pathway such that they are able to enter the cytoplasm where intracellular pathways exist to traffic the nanoparticles to the nucleus, is rare (<1%). Therefore, the majority of the therapeutic cargo ends up in the lysosome whose highly acidic and enzyme-rich environment leads to their degradation. By directly distributing the therapeutic molecules (siRNA), model molecules (such as different molecular weights dextrans) or nanoparticles (citrate capped gold nanoparticles) throughout the cytosol, the method according to the present invention thus facilitates a direct pathway that specifically avoids these organelles, thereby allowing enhanced uptake of the therapeutic cargo in the nucleus. This, in turn, leads to improved transfection efficiencies without necessitating complex strategies to affect the endosomal/lysosomal escape. As such, the method according to the present invention constitutes an ex vivo technique that allows rapid, instantaneous delivery of the desired therapeutic agent with the possibility for transient control to re-engineer target cells isolated from the blood or tissue of a patient in the laboratory, which is then infused back into the same patient.

Figure 1A:
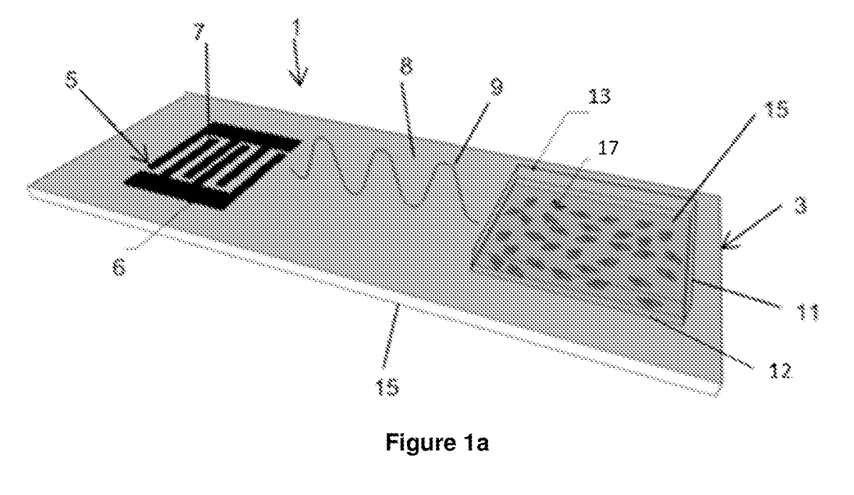
FIG. 1a is a schematic view of an acoustically-mediated intracellular transfer device according to the present invention.

The acoustic wave energy device 1 according to the present invention is set up as illustrated in FIG. 1a. The device 1 includes a piezoelectric substrate 3, in this case, lithium niobate (LiNbO$_3$), on which electrodes 6 of an interdigitated transducer (IDT) 5 are photolithographically patterned on a working surface 8 thereof. The width and the gap of the IDT fingers 7 of the electrodes 6 determines the wavelength and hence its resonant frequency. In the present case, a wavelength of 132 μm corresponding to a frequency of 30 MHz was employed, although any SAW frequency from 10 MHz and above can, in principle, be used. Applying an alternating electrical signal to the IDT electrodes 6 at this resonant frequency with the aid of a signal generator and amplifier (not shown) then launches the surface acoustic waves (SAW) 9 that propagate as a Rayleigh wave along the working surface 8 of the substrate 3 upon which the IDT electrodes 6 are positioned.

In addition to the SAW 9, surface reflected bulk waves (SRBW) can also propagate internally within the substrate 3 between the working surface 8, and an adjacent opposing surface 15 of the substrate 3. The SRBW is internally reflected between the working surface 8 and the opposing surface 15 and preferably also provides acoustic wave energy for the device 1. The propagation of the SRBW may be enhanced by configuring the substrate 3 so that it has a thickness that is approximately equal to the SAW wavelength. Further description of SRBWs can be found in International Publication No. WO2016/179664 (RMIT University).

The device 1 further includes a receptacle in the form of a well plate 11, preferably (although not necessarily limited to) with a base 12 and side walls 13 made from glass or other acoustically transmitting materials such as acrylic, resting on the substrate surface 8, and having multiple wells for accommodating therein a cell media 15. Alternative receptacles such as petri dishes, transwell culture plates, microarray plates, cell flack and other standard laboratory items for cell culture made from glass or other materials could be used. It is also envisaged that a receptacle having side walls only and no base wall be used so that the cells can be in direct contact with (i.e., directly coupled to) the working surface 8. The cell media 15 includes a plurality of cells 17, and therapeutic molecules/nanoparticles that will be transferred during the intracellular delivery into the cells 17. The position of the well plate 11 couples the acoustic wave energy of the SAW 9 and preferably SRBW to the accommodated cells 17. A thin layer of silicone oil (or another fluid couplant, including water, glycerine, or other acoustic transmitting materials including gels and tapes) placed between the working surface 8 and base wall 12 of the well plate 11 aids the coupling of the acoustic wave energy into the wells and minimises the acoustic impedance mismatch. The cells 17 (as a model, human embryonic kidney cells (HEK 293-T and HeLa) were used) and their constituent media, to which the therapeutic molecules/nanoparticles are added, are then exposed to the acoustic radiation for a specific duration (minutes), after which the uptake of the molecules/nanoparticles within the cells 17 can be evaluated. In this case, 10 nm gold nanoparticles, different molecular weight dextrans (20 kDa, 70 kDa and 250 kDa molecules) or short interfering ribonucleic acid (siRNA) were used as the molecules/nanoparticles.

Figure 1B:
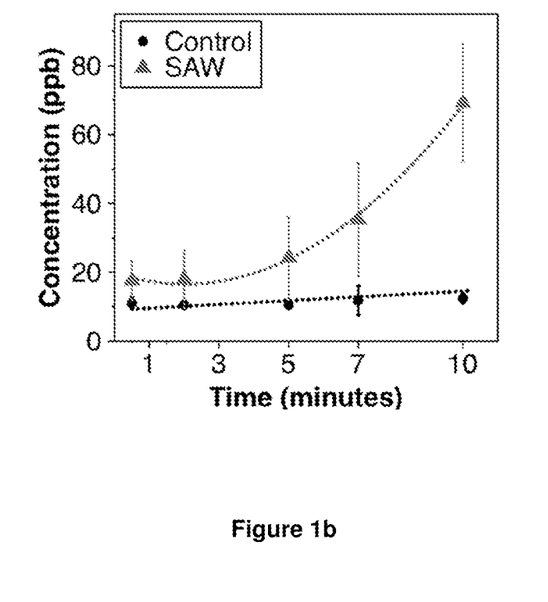
FIG. 1b is a graph showing the quantitative measurements of the internal cell nanoparticle concentration using inductively-coupled mass spectrometry (ICP-MS)
Figure 1C:
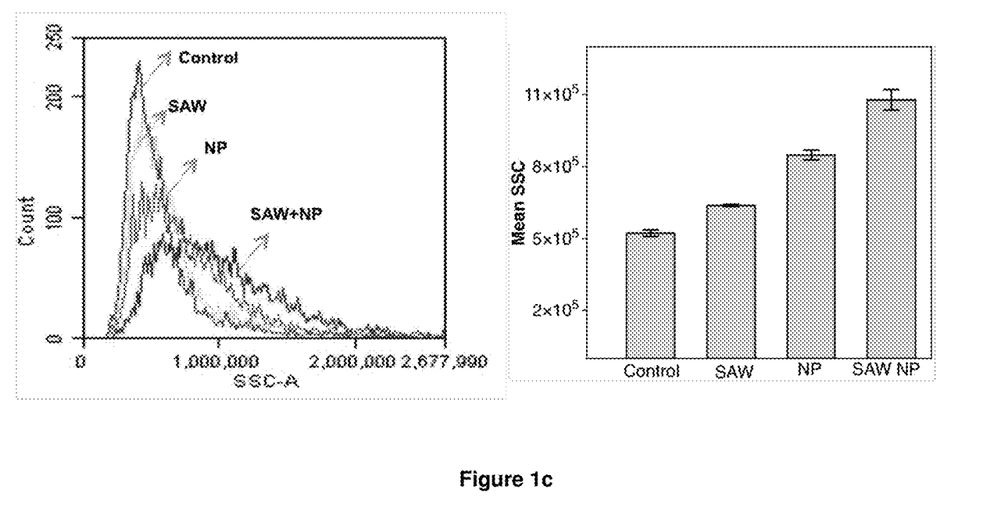
FIG. 1c are graphs showing the quantitative measurements of the internal cell nanoparticle concentration using flow cytometry (FACS) when exposed to a SAW for 5 minutes.
Figure 1D:
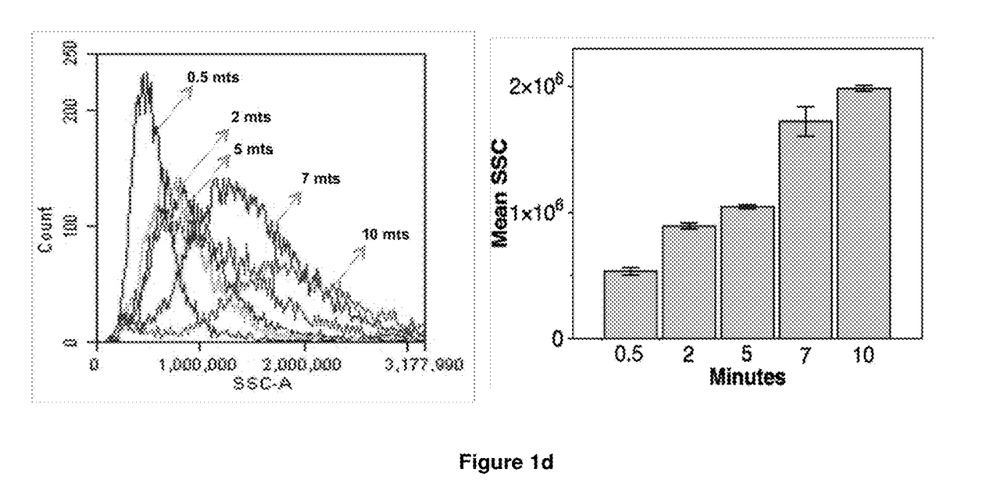
FIG. 1d are graphs showing the quantitative measurements of the internal cell nanoparticle concentration using flow cytometry (FACS) showing the effect of exposure time.

It is noted from the quantitative measurements of the internal cell nanoparticle concentration using inductively-coupled mass spectrometry (ICP-MS) in FIG. 1*b* that there is considerably enhanced levels of cellular nanoparticle uptake compared to the case in which nanoparticle internalisation occurred passively in the absence of external forcing. This is confirmed via flow cytometry (FACS) wherein it can be seen in FIG. 1*c* that the side scatter increases due to the difference in cell density with increasing uptake. The nanoparticle concentration is observed to increase with the exposure time (FIG. 1*b, d*), the almost two-fold enhancement in the uptake after a mere 30 seconds almost quadrupling over 10 mins. This nonlinear departure from the slow and gradual linear change in the nanoparticle uptake for the passive uptake (despite incubation of the cells over 4 hours in the presence of the nanoparticles) highlights the significance of the exposure of the cells to acoustic wave energy, and strongly suggests a distinct mechanism in which the acoustic wave energy induces a different internalisation pathway compared to that if the nanoparticles were allowed to be taken up by the cells passively.

Figure 2:
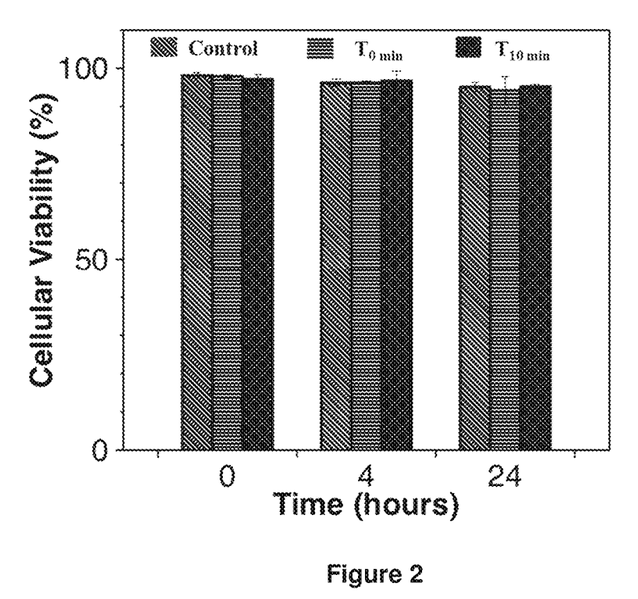
FIG. 2 is a graph showing cellular viability in an MTT assay.
Figure 3:
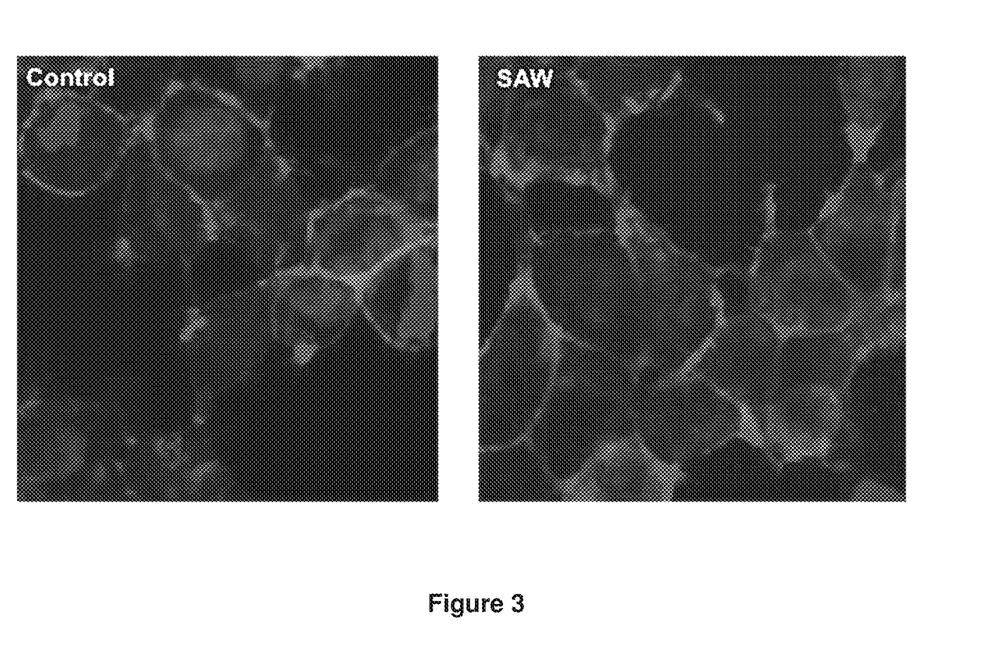
FIG. 3 are confocal microscopy images of the cytoskeleton, actin network and nucleus of the cells.
Figure 4:
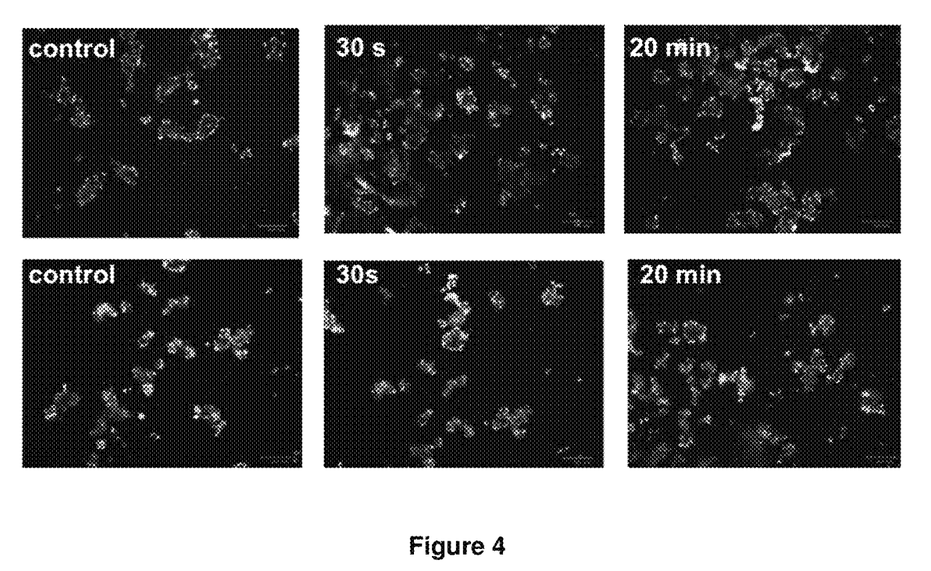
FIG. 4 are images showing the effect over time of the SAW on the mitochondrial membrane potential using JC-1 dye.
Figure 5:
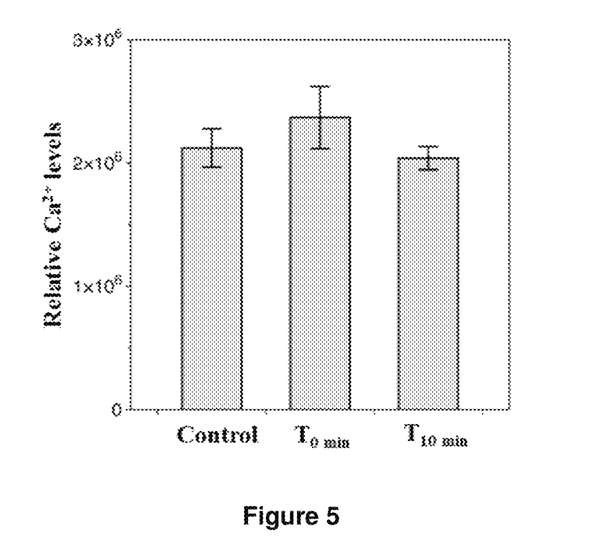
FIG. 5 is a Fura-2AM calcium flux assay graph showing the calcium flux into the cells at the start of the experiment (T0) and after 10 minutes (T10) of SAW exposure compared to the control when no acoustic wave excitation is applied.

Regardless of the exposure duration, surprisingly few detrimental effects to the cell viability were observed, as seen from the results of the MTT assay in FIG. 2. The figure shows an exposure duration of 5 minutes, with results acquired at three time points, 0, 4 and 24 hours post-exposure to the acoustic radiation. Over 97% of the cells are seen to remain viable post-treatment, which is significantly higher than the majority of other membrane-disruption-mediated delivery methods, particularly sonoporation. By comparison, conventional BAW excitation, whose excitation frequencies are generally in the Hz to kHz range, and never exceeding 5 MHz, the higher frequencies used in the present invention considerably lower the power (by approximately one to two orders of magnitude in comparison) employed. This not only significantly reduces heating (temperature increases no greater than approximately 37-39° C. were observed even after 10 minutes of acoustic wave energy exposure), but completely suppresses any cavitation events that impose significant stresses on the cell membrane to the point of the creation of pores. Moreover, at such high frequencies, the applied electric and hence acoustic field reverses too quickly compared to the molecular relaxation time scale such that macromolecules such as peptides and proteins are almost never degraded by the acoustic wave energy, even at significantly larger powers than those employed here. Further confirmation of the post-exposure cell viability can be seen from close inspection of the confocal microscopy images of the cytoskeleton, actin network and nucleus of the cells, as well as results from the trypan blue assay, which indicated a high (>90%) retention of the post-seeding efficiency (FIG. 3). This is complemented by measurement of the mitochondrial membrane potential (MMP) and the calcium flux levels across the cell membrane, which play a vital role in stress-induced apoptosis. In the former, the negligible difference between the depolarised to hyperpolarised MMP, which provides an indication of anomalies in the cell structure, in cells that were both unexposed (control) and exposed to the acoustic wave energy (FIG. 4) suggests that the acoustic wave energy has negligible effect on the mitochondrial membrane potential. In the latter, the results from the Fura-2AM assay in FIG. 5 show an increase in the calcium flux into the cells immediately upon exposure to the acoustic radiation. However, this returned to baseline values 10 minutes after relaxation of the acoustic wave energy excitation, suggesting fast resealing of the cell membrane and hence cell recovery following its disruption by the high frequency acoustic forcing. This thus explains why high post-exposure cellular viabilities are sustained. The underlying nanoparticle internalisation mechanism that facilitates this fast resealing and healing will now be described.

Figure 6:
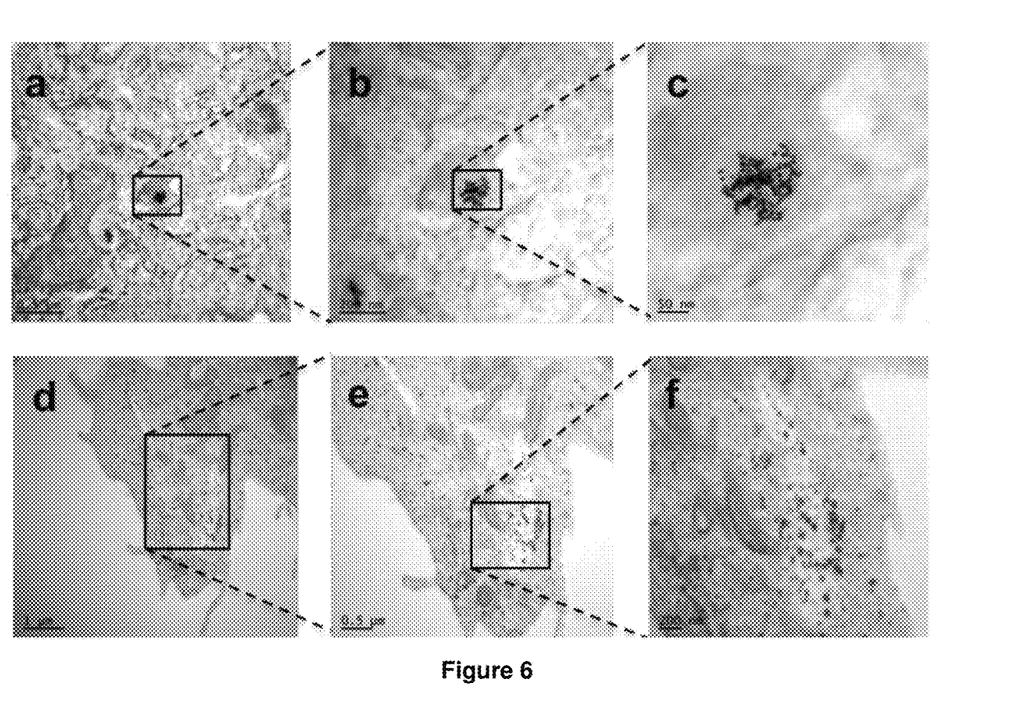
FIGS. 6a to 6f are transmission electron microscopy (TEM) images, with 6a to 6c being control samples, and 6d to 6f being acoustic wave energy exposed samples showing the internalised nanoparticles to be uniformly distributed throughout the cytosol when their uptake is mediated by the acoustic wave energy irradiation.
Figure 7:
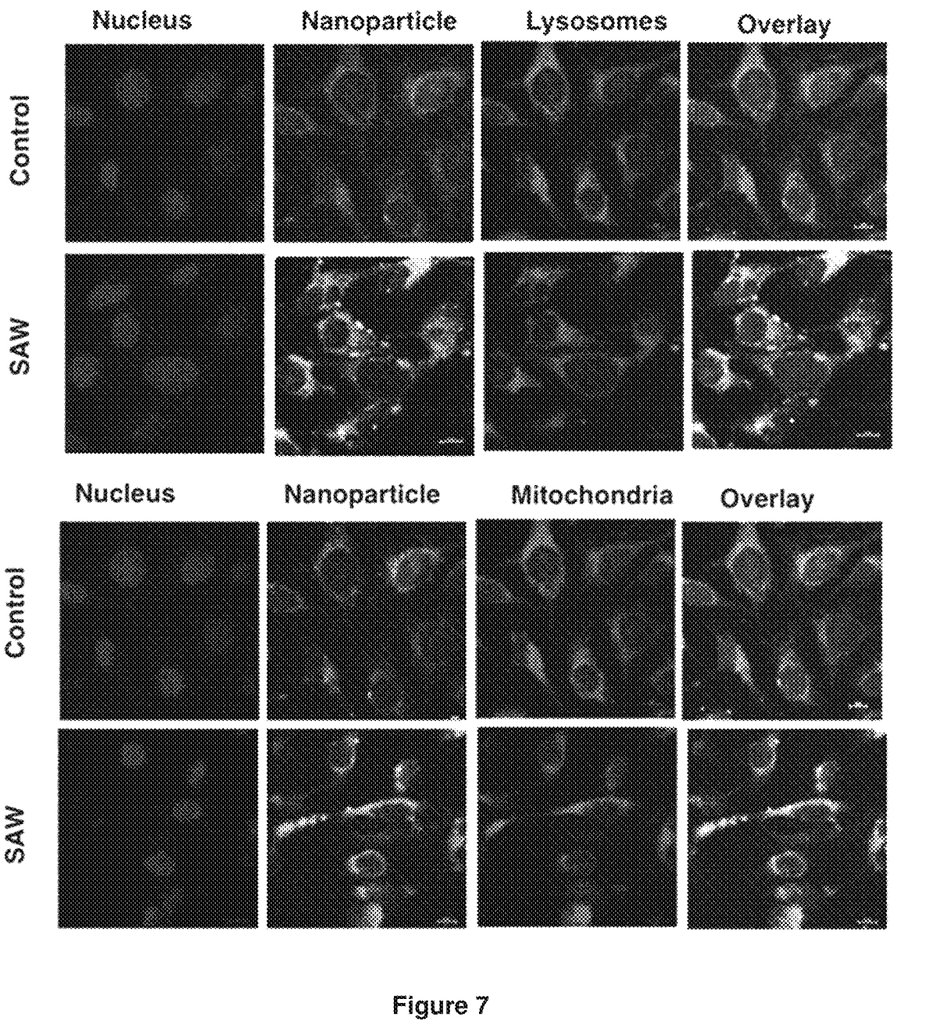
FIG. 7 are confocal images showing the lysosomes and mitochondria within control and acoustic wave energy exposed cells.
Figure 8:
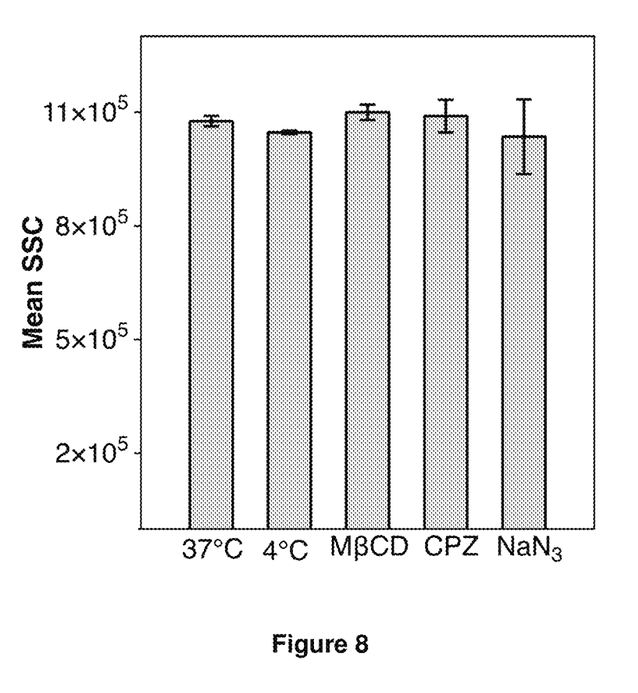
FIG. 8 shows the effect of different chemical as well as the environmental inhibitors on the receptor mediated endocytosis pathway in the presence of SAW for 5 minutes.

In addition to enhanced levels in cellular nanoparticle uptake, it was observed that the internalised nanoparticles were uniformly distributed throughout the cytosol when their uptake is mediated by the acoustic wave energy irradiation, as observed by the transmission electron microscopy (TEM) images in FIG. 6. FIGS. 6*a* through 6*c* show a controlled sample where no acoustic wave energy irradiation was applied and the nanoparticles are consequently aggregated. In contrast, FIGS. 6*d* through 6*f* shows very clearly that the nanoparticles are uniformly distributed through the cytosol when their uptake is mediated by the acoustic wave energy irradiation. Moreover, the confocal images in FIG. 7, which were stained for the mitochondria and lysosomes, clearly show that the nanoparticles are not just internalised within the organelles but also distributed throughout the cytosol. This is in complete contrast to the control experiment in the absence of acoustic wave energy irradiation where the nanoparticles are observed to be localised within specific organelles such as the endosomes and lysosomes;

this is seen from the overlay between the nanoparticles and the stained organelles. These observations are not just significant in terms of their implication for avoiding localisation within the endosomal and hence lysosomal compartments, which lead to significant degradation of the cargo. They also shed light on the existence of an alternate mechanism for the internalisation of the nanoparticles that does not follow the endocytotic pathway. This is confirmed by the use of chemical inhibitors such as chlorpromazine, methyl-β-cyclodextrin and sodium azide ($NaN_3$) as well as environmental inhibitor by performing the experiments at 4° C., to block the receptor-mediated pathways. The chemical and environmental inhibitors were introduced to rule out the possibility of the involvement of endocytosis in the internalisation of nanoparticles. In all of these cases, no discernible drop in the nanoparticle internalisation under acoustic wave energy excitation is observed (FIG. 8).

Figure 9:
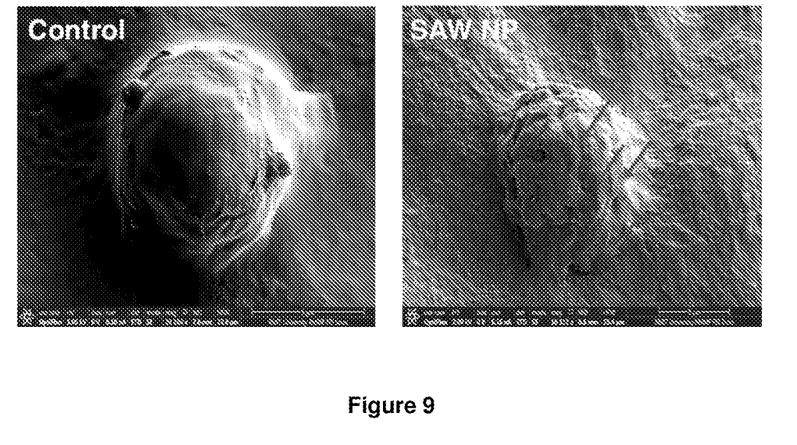
FIG. 9 shows scanning electron microscopy (SEM) images respectively for the control experiment in the absence of the acoustic excitation, and of cells exposed to the acoustic wave energy radiation.
Figure 10:
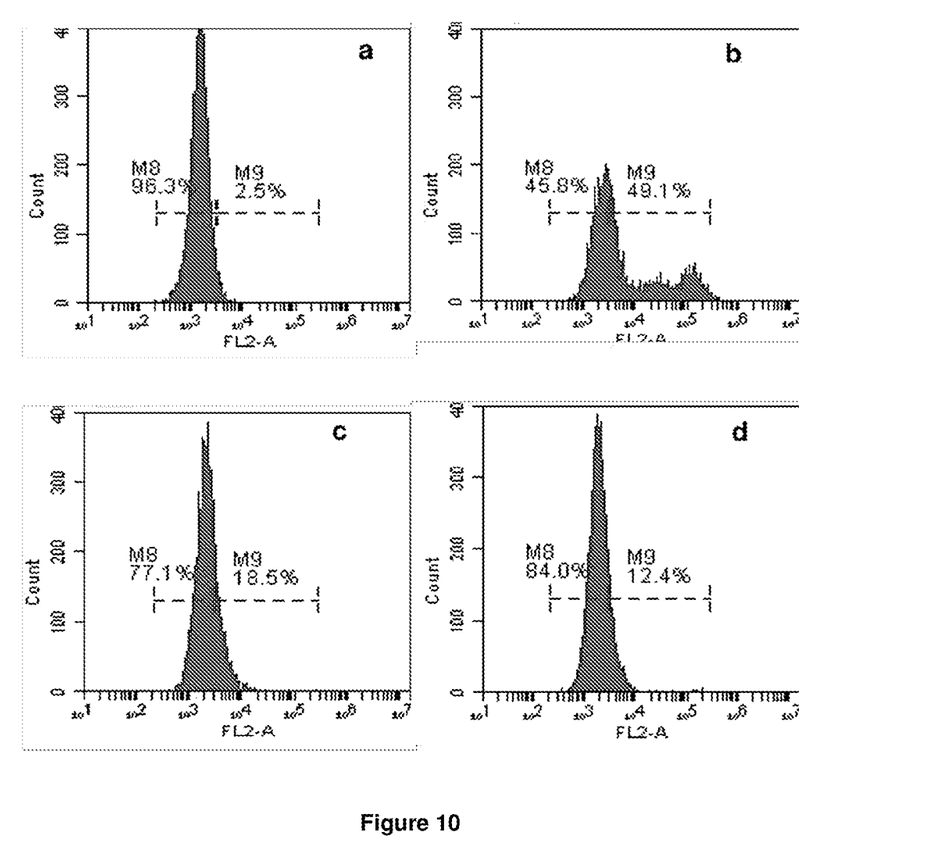
FIGS. 10a to 10d are graphs showing the results from propidium iodide (PI) uptake experiments.

Given that endocytosis plays little or no role in the acoustically-mediated nanoparticle uptake, attention was turned to the possibility of membrane-disruption under the acoustic forcing. Unlike sonoporation, however, the formation of any significant pore formation as seen in the scanning electron microscopy (SEM) images in FIG. 9 was not observed. On the contrary, the presence of various submicron indentations were apparent, although only when the cells were fixed under 4% formaldehyde during acoustic wave energy exposure to 'freeze' their existence; in the absence of a fixative, these indentations, which are referred to as 'nanopores', to distinguish it from the large physical (macro)pores (typically 1-2 µm), were not observed even when the cells were imaged immediately when the acoustic excitation was relaxed. The transient nature of these nanopores is substantiated by the results from the propidium iodide (PI) uptake experiments shown in FIG. 10 where it can be seen that the PI uptake into the cell in the presence of acoustic excitation (FIG. 10*b*) increases by almost 50% as compared to that of control samples (FIG. 10*a*), indicating a large diffusive flux through these transient nanopores. However, when these experiments were repeated with the application of SAW without any PI, followed by the addition of PI immediately after the acoustic wave removal ($T_0$) the amount of PI internalised in the cell rapidly decreases to approximately 20% (FIG. 10*c*) indicating the rapid closure of nanopores. Addition of PI ten minutes ($T_{10}$) after removal of the acoustic wave excitation led to a further decrease of PI in the cells to almost 12% (FIG. 10*d*). The extremely short transient nature of these micropores therefore further warrants significant distinction from the pores formed during poration. This is because the latter (macro)pores typically recover over many minutes, if at all. This is clearly also absent from the results for the MTT assay on cell viability in FIG. 2 where it can be seen that no further cell recovery occurs with time (over many minutes) beyond an immediate sealing of the micropores upon cessation of the acoustic wave energy excitation.

Such absence of (macro)pores is perhaps unsurprising given the absence of cavitation events required to drive pore formation at the acoustic wave energy excitation frequencies and powers used, let alone even at much higher powers when nebulisation ensues. Rather, the inventors hypothesise that the low amplitude yet high frequency sound wave excitation is sufficient to disrupt the lipid structure that make up the cell membrane to sufficiently induce transient gaps between the lipid molecules that are large enough to facilitate diffusional translocation of the nanoparticles through them but considerably smaller than the physical pores crested by conventional electroporation or sonoparation methods.

Figure 11:
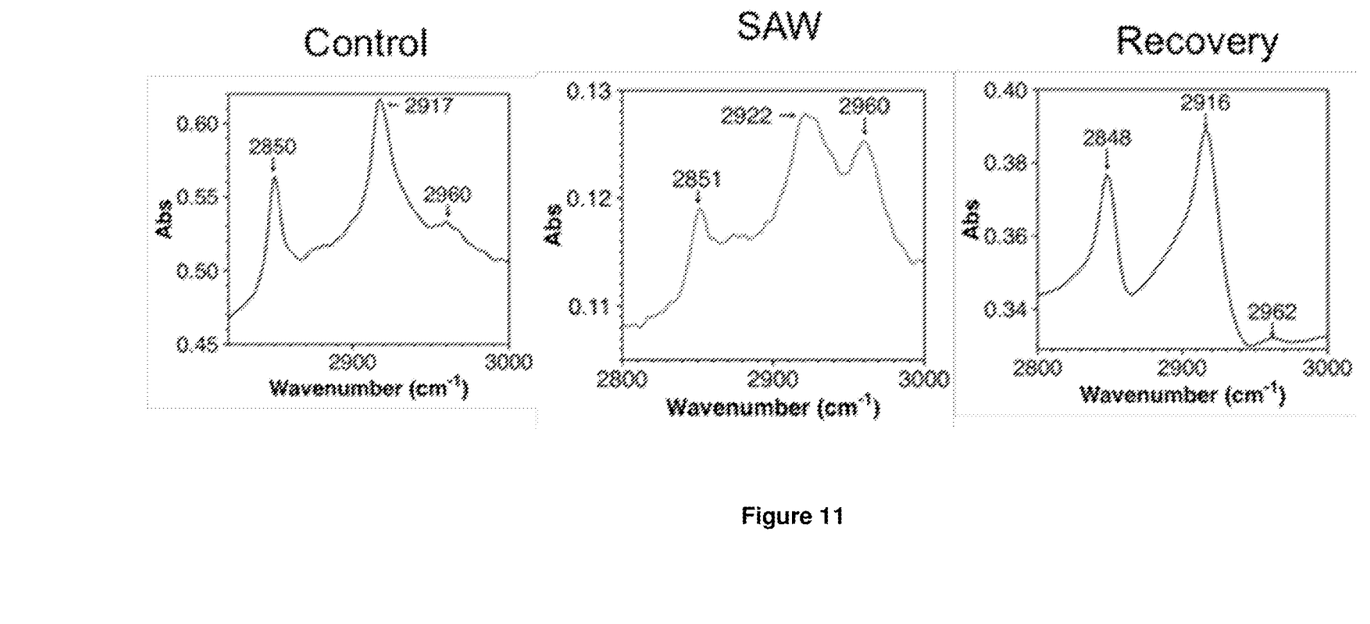
FIG. 11 show Fourier Transform Infrared (FTIR) spectra showing a change in the organisation of the lipid structure upon acoustic excitation of the cells.
Figure 12:
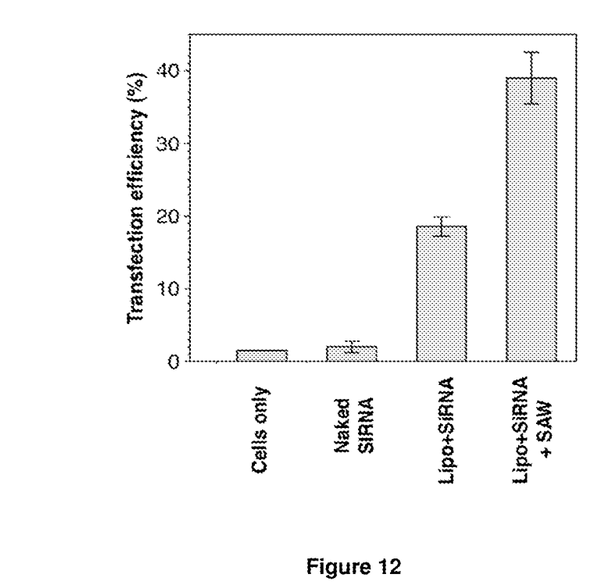
FIG. 12 shows the efficiency of SAW mediated fluorescence (Cy3) labelled GAPDH siRNA transfection in HeLa cells.
Figure 13:
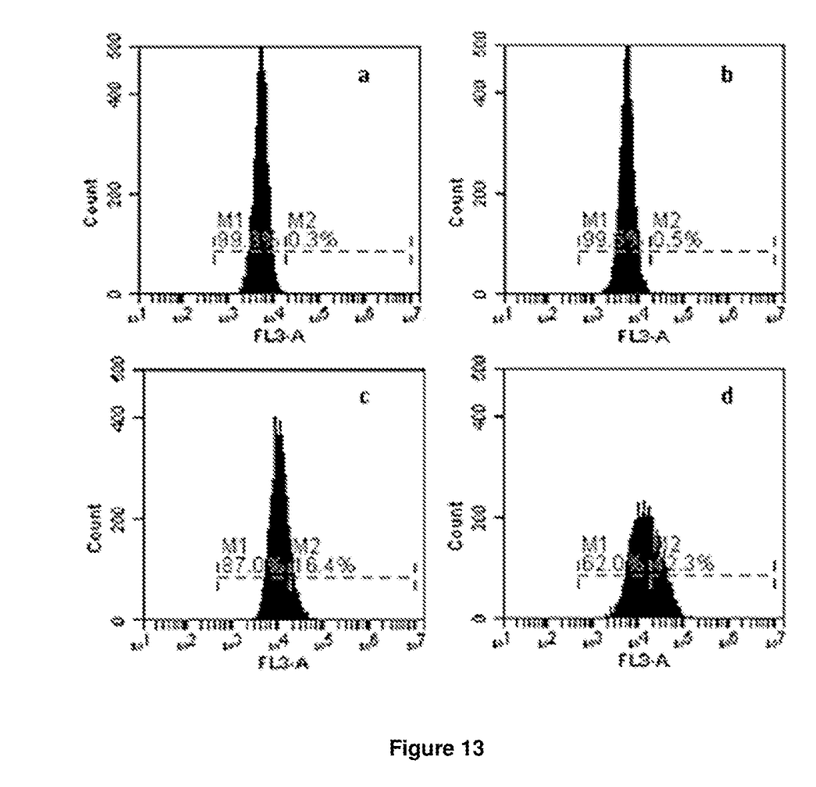
FIGS. 13a to 13d show the flow cytometry graphs of the transfection efficiencies of control (FIG. 13a), naked siRNA (FIG. 13b), a combination of lipofectamine and siRNA (FIG. 13c) and a combination of lipofectamine, siRNA and SAW (FIG. 13d)

This is not without precedent given that mechanical oscillating a cell even at sub-kHz frequencies has been observed to disrupt the cell membrane to increase its permeability, and, more relevantly, SAWs at comparable frequencies to that employed in the present work have been shown to induce structural alterations to lipid structure that involves changes in the tilt of the lipid headgroups from equilibrium. The Fourier Transform Infrared (FTIR) spectrum shown in FIG. 11 indeed indicates a change in the organisation of the lipid structure upon acoustic excitation of the cells.

Further, the inventors have demonstrated acoustic enhancement of cellular transfection with nucleic acids in which they observe internalisation of Cy3-labeled GAPDH siRNA with lipofectamine as a transfection agent. This showed a two-fold increase into the cell in the presence of SAW compared to the control with the same transfection parameters, as quantified using flow cytometry (FIG. 12 and FIGS. 13*a* through 13*d*).

Figure 14:
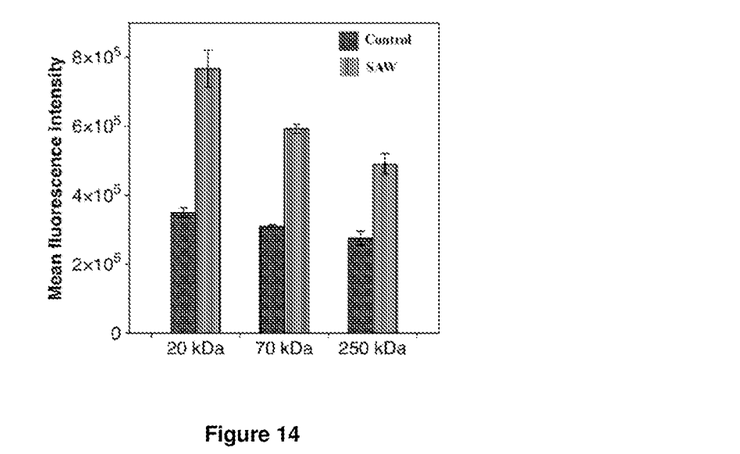
FIG. 14 shows the delivery efficiencies of different dextran molecules delivered using SAW.
Figure 15:
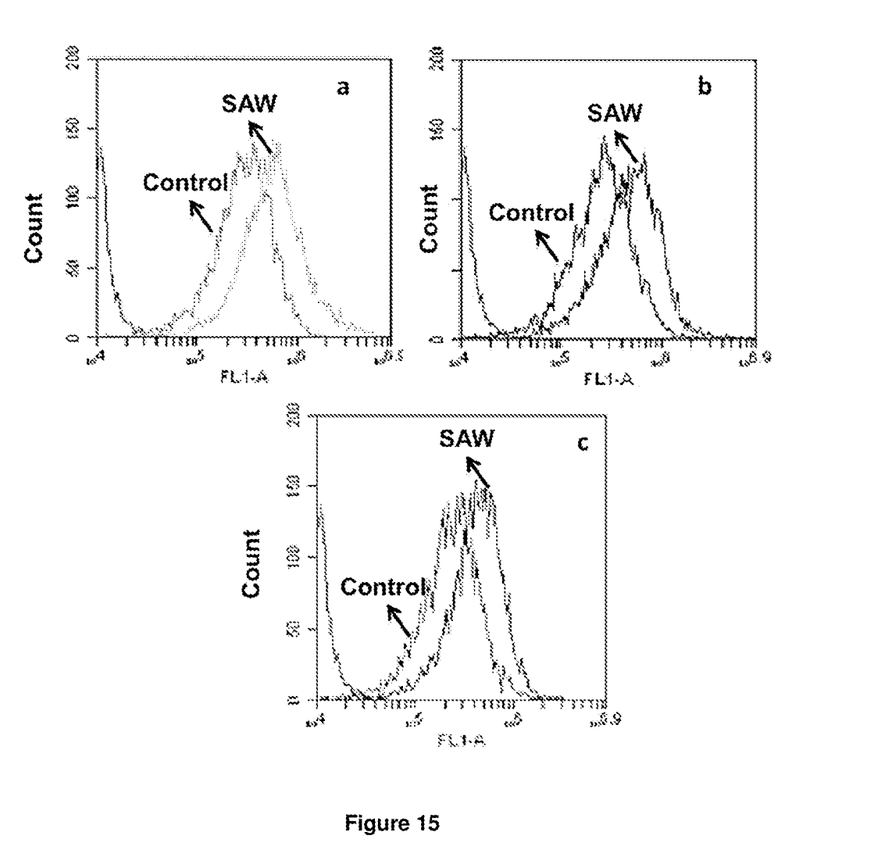
FIGS. 15a to 15c show the increase in the intracellular delivery of FITC labelled dextran with molecular weights of 20 kDa (FIG. 15a), 70 kDa (FIG. 15b) and 250 kDa (FIG. 15c) using flow cytometry.

In addition to enhancing cellular nanoparticle uptake, the SAW mediated delivery method was also demonstrated for the delivery of other molecules to cells by using model fluorescently labelled dextran molecules of varying molecular weights (20 kDa, 70 kDa, and 250 kDa). FIG. 14 shows a significantly higher perfusion rate of dextran molecules in the presence of SAW in contrast to the control. The inventors note that the delivery of molecules to the cells with the lowest molecular weight used (20 kDa) is higher than those with a higher molecular weight, 250 kDa, as expected (FIG. 14 and FIGS. 15*a-c*).

Figure 16:
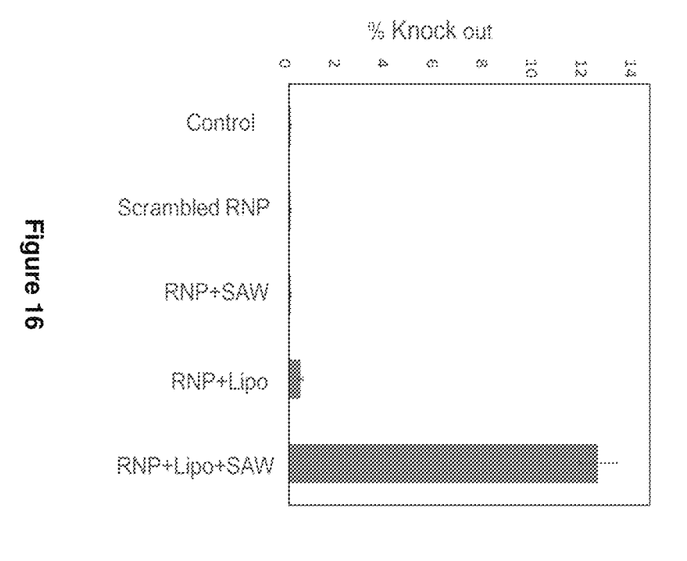
FIG. 16 shows knockout percentage of CCR5 gene from measurements of the fluorescence intensity using flow cytometry. Specifically, FIG. 16 indicates the percentage of knockout of CCR5 gene in sham control, scrambled RNP (non-targeting negative control), RNP+SAW (sgRNA, Cas9 and SAW), RNP+Lipo (sgRNA, Cas9 and Lipofectamine-CRISPRmax), RNP+Lipo+SAW (sgRNA, Cas9, LipofectamineCRISPRmax and SAW).

The SAW mediated delivery method was further extended to the delivery of CRISPR-Cas9 gene editing system in suspension cells (FIG. 16). Deletion of a portion of the CCR5 gene (chemokine receptor type 5), has shown an improved resistance towards HIV-1 infection and hence was chosen as a model to show SAW mediated delivery of ribonucleoprotein (RNP) complex to knockout CCR5 gene. HUT-78 cell lines, cutaneous human T-cell lymphocytes expressing the gene were exposed to acoustic radiation (30 MHz) using a focused IDT design electrode. The transfection was carried out using the ribonucleoprotein complex (RNP) consisting of an in vitro assembled Cas9 protein and guide RNA targeting CCR5 loci. The transfection was accompanied with the use of commercially available lipid-based system, lipofectamine CRISPRmax. The knockout efficiency was obtained 48 hours after transfection with the help of flow cytometry. The samples were incubated with FITC labelled anti-CCR5 antibody to correlate the reduction in fluorescence with the number of CCR5 receptors on cell surface and thus decipher the knockout percentage. The acoustically irradiated samples showed ~12% reduction in CCR5 florescence as compared to that of the control samples (FIG. 16). The control sample comprised of the RNP complex and lipofectamine CRISPRmax while the acoustically irradiated samples consisted of SAW in addition to all the components present in the control samples. The sgRNA sequences used are ATGTGGAAGT-CACGCCCGTT<u>GGG</u> and GCAGTTGTGTGACACG-GAAG<u>CGG</u>.

The inventors have clearly and successfully demonstrated driving individually each of nanoparticles, dextran, nucleic acids (including siRNA and sgRNA), as well as and other biologics or therapeutic molecules (including proteins and lipid complexes such as Cas9 and Lipofectamine CRISPRmax) into cells as outlined above. The uptake of these nanoparticles and molecules within the cells could then be evaluated.

Modifications and variations as would be deemed obvious to the person skilled in the art are included within the ambit of the present invention as claimed in the appended claims.

The invention claimed is:

1. An intracellular delivery device including, a piezoelectric substrate having a working surface, at least one interdigitated transducer located on and in contact with the working surface, and a receptacle located on the working surface for accommodating a cell media;
   the cell media comprising a plurality of cells to be targeted for intracellular delivery; and
   therapeutic molecules or nanoparticles to be transferred by intracellular delivery into the cells;
   wherein an alternating signal applied to the interdigitated transducer generates acoustic wave energy through the piezoelectric substrate that can be transferred to the plurality of cells at a frequency which avoids sonoporation involving membrane disrupting cavitation events near the plurality of cells.

2. The intracellular delivery device according to claim 1, wherein the acoustic wave energy is propagated as a surface acoustic wave along the working surface.

3. The intracellular delivery device according to claim 2, wherein the acoustic wave energy is further propagated as a surface reflected bulk wave within the piezoelectric substrate and internally reflected between the working surface and an adjacent surface of the piezoelectric substrate.

4. The intracellular delivery device according to claim 1, wherein the at least one interdigitated transducer is adapted to propagate surface acoustic waves having a frequency of greater than 10 MHz.

5. The intracellular delivery device according to claim 4, wherein the at least one interdigitated transducer is adapted to propagate surface acoustic waves having a frequency of about 30 MHz.

6. The intracellular delivery device according to claim 1, wherein the receptacle has a base wall acoustically coupled to the working surface.

7. The intracellular delivery device according to claim 6, further including a coupling medium between the working surface and the receptacle base wall to facilitate acoustic coupling therebetween.

8. The intracellular delivery device according to claim 7, wherein the coupling medium is an acoustic fluid, gel or tape couplant.

9. The intracellular delivery device according to claim 8, wherein the coupling medium is a thin layer of silicone oil.

10. The intracellular delivery device according to claim 1, wherein the receptacle includes a plurality of wells for accommodating therein the cell media.

11. The intracellular delivery device according to claim 1, wherein the working surface is configured to directly contact the cell media.

12. The intracellular delivery device according to claim 1, wherein the piezoelectric substrate is formed from lithium niobate ($LiNbO_3$).

13. An intracellular delivery method comprising:
    exposing a cell media to acoustic wave energy including surface acoustic waves, the cell media comprising a plurality of cells and therapeutic molecules and/or nanoparticles;
    wherein the therapeutic molecules and/or nanoparticles are transferred into the exposed cells by intracellular delivery,
    further wherein the acoustic wave energy including surface acoustic waves is at a frequency which avoids sonoporation involving membrane disrupting cavitation events near the plurality of cells.

14. The intracellular delivery method according to claim 13, wherein the therapeutic molecules include nucleic acids and transfecting agents.

15. The intracellular delivery method according to claim 13, wherein the acoustic wave energy further includes surface reflected bulk waves.

16. The intracellular delivery method according to claim 13, including exposing the cell media to acoustic energy generated by surface acoustic waves having a frequency greater than 10 MHz.

17. The intracellular delivery method according to claim 13, including exposing the cell media to acoustic energy generated by surface acoustic waves having a frequency of about 30 MHz.

18. The intracellular delivery method according to claim 13, including exposing the cell media to acoustic wave energy for at least 30 seconds.

19. The intracellular delivery method according to claim 13, including exposing the cell media to acoustic wave energy for 5 minutes.

20. The intracellular delivery method according to claim 13, including exposing the cell media to acoustic wave energy for 10 minutes.

* * * * *